United States Patent [19]
Barany et al.

[11] Patent Number: 5,196,566
[45] Date of Patent: Mar. 23, 1993

[54] HYPERSENSITIVE ACID-LABILE HANDLE FOR SOLID-PHASE PEPTIDE SYNTHESIS

[75] Inventors: George Barany, Falcon Heights, Minn.; Fernando Albericio, Barcelona, Spain

[73] Assignee: Regents of the University of Minnesota, Minneapolis, Minn.

[21] Appl. No.: 576,233

[22] Filed: Aug. 31, 1990

[51] Int. Cl.$^5$ ............................................. C07C 69/76
[52] U.S. Cl. ..................................... 560/61; 560/62; 558/242; 564/164; 564/165; 548/378
[58] Field of Search ................... 560/61, 62; 558/242; 564/164, 165; 548/369.4

[56] References Cited

PUBLICATIONS

Florsheimer, A. and B. Riniker, *Proceedings of the European Peptide Symposium* Abstract 95, (Sep. 1990).
Albericio, F. and G. Barany, *Tetrahedron Letters* 32:1015–1018 (1991).
Durr H. et al., *Proceedings of the European Peptide Symposium* Abstract 96, (Sep. 1990).
Albericio, F. et al., *J. Organ. Chem.* 55:3730–3743 (1990).
Barany et al., *Int. J. Peptide Protein Res.* 30:703–739 (1987).
Sheppard and Williams, *J. Chem. Soc. Chem. Commun.* 587–589 (1982).
Mergler et al., *Tetrahedron Letter* 29:4009–4012 (1988).
Albericio et al., *Forum Peptides* (1984).
Albericio and Barany, *Int. J. Peptide Protein Res.* 30:206–216 (1987).

*Primary Examiner*—Paul J. Killos
*Attorney, Agent, or Firm*—Hamilton, Brook, Smith & Reynolds

[57] ABSTRACT

Novel acid-labile tris(alkoxy)benzyl ester handles for use in linking protected amino acid or peptides to a support during peptide synthesis are disclosed. Methods for producing the handles, for linking them to solid support resins and for using the resin-linked handles in peptide synthesis are disclosed.

5 Claims, 2 Drawing Sheets

FIG. I

HYPERSENSITIVE ACID-LABILE HANDLE FOR SOLID-PHASE PEPTIDE SYNTHESIS

GOVERNMENT SUPPORT

This invention was made with government support under GM 42722 awarded by the National Institutes of Health. The government has certain rights in the invention.

BACKGROUND OF THE INVENTION

Partially protected peptide segments are often required as intermediates for the preparation of larger peptides or small proteins by segment condensation approaches, either in solution or on a polymeric support. F.M. Finn and K. Hofmann, *In: The Proteins*, 3rd Ed., Vol. 2., H. Neurath and R.L. Hills (eds.), Academic Press, N.Y. pp. 105–253 (1976); G. Barany et al., *Int. J. Peptide Protein Res.*, 30:705–739 (1987) Solid-phase synthesis is widely acknowledged to offer the best prospects for rapid and efficient assembly of peptide chains, but until relatively recently, the needed levels of selectivity in conditions for deprotection of the $N^\alpha$-amino group and side-chains of amino acids, and in procedures for detachment of peptides from the support, have not been available. Such conditions require that a peptide can be cleaved successfully to furnish a free $C^\alpha$-carboxyl group with all other functional groups remaining protected, and that the resultant intermediate can be purified before its further use in segment condensation. T. Kubiak et al., *Biochemistry*, 26:7849–7855 (1987); N. Kneib-Cordonier et al., *Int. J. Peptide Protein Res.*, 35:527–538 (1990); G.B. Field and R.L. Noble, *Int. J. Peptide Protein Res.*, 35:161–214 (1990).

In recent years, a strategy employing the orthogonal combination of base-labile 9-fluorenylmethyloxycarbonyl (Fmoc) for $N^\alpha$-amino protection and acid-labile tert-butyl (tBu) derivatives for side-chain protection has been used. An "orthogonal" system is defined as one using two or more independent classes of protecting groups that are removed by different chemical mechanisms. This combination avoids the relatively harsh final cleavage conditions of the more conventional strategy based on the graduated lability to acid of tert-butyloxycarbonyl (Boc) for $N^\alpha$-amino protection and benzyl or cyclohexyl derivatives for side-chain protection. In the Fmoc/tBu strategy, a third dimension of orthogonality can be provided by use of ortho-nitrobenzyl (photolabile), silicon-containing (fluoride-labile), or allyl-derived (cleaved with Pd(O)) anchoring linkages. R. Ramage et al., *Tetrahedron Lett.*, 28:4105–4108 (1987); D.G. Mullen and G. Barany, *J. Org. Chem.*, 53:5240–5248 (1988); H. Kunz and B. Dombo, *Agnew. Chem. Int. Ed. Engl.*, 27:711–713 (1988); B. Blankemeyer-Menge and R. Frank, *Tetrahedron Lett.*, 28:5871–5874 (1988). However, the aforementioned orthogonally cleavable anchors are prepared by multi-step routes, and in some cases, cannot be satisfactorily applied to solid-phase synthesis of protected peptide segments.

An alternative approach utilizes anchoring linkages, or handles, that are cleaved with extremely dilute acid. This strategy requires exquisite "fine-tuning" of the anchor structure and the corresponding removal conditions. For example, a (4-hydroxymethyl-3-methoxyphenoxy)acetic acid handle and the closely related 2-methoxy-4-alkoxybenzyl alcohol (SASRIN) support have been used and lead to bis(alkoxy)benzyl ester anchoring linkages which cleave with 1% (v/v) trifluoroacetic acid (TFA) in dichloromethane. E. Atherton et al., *In: Solid Phase Peptide Synthesis*, IRL Press Oxford, U.K. (1989); R.C. Sheppard and B.J. Williams *J. Chem. Soc. Chem. Commun.*, pp. 587–589 (1982); M. Mergler et al., *Tetrahedron Lett.*, 29:4009–4012 (1988). These cleavage conditions promote premature side-chain deprotection at Lys(Boc) and Tyr(tBu), however. R.C. Sheppard and B.J. Williams, *J. Chem. Soc. Chem. Commun.*, ibid. Other systems using a trialkoxydiphenylmethyl ester handle or an ortho-chlorotrityl handle lead to esters which cleave with 10% (v/v) acetic acid in dichloromethane, but also cleave prematurely in the presence of a free $C^\alpha$-carboxyl group of an incoming protected amino acid during each coupling step. H. Rink, *Tetrahedron Lett.*, 28:3787–3790 (1987); K. Barlos et al., *Tetrahedron Lett.*, 80:3943–3946 (1989). A handle which permits efficient cleavage of a peptide from the solid support, without causing deprotection of side-chain groups or $N^\alpha$ terminal groups, would be valuable for preparing protected peptide intermediates and for other applications where deprotection is not desired.

SUMMARY OF THE INVENTION

The invention relates to novel compounds, which are precursors or derivatives of a tris(alkoxy)benzyl ester having the formula:

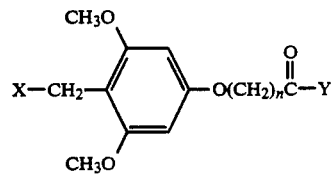

wherein n is from about 1 to about 10, X is OH, a halogen or an α-carboxyl group of a protected amino acid or peptide, and Y is selected from the group consisting of: an active ester, thioester or amide. Y also represents the amide linkage to an amino-functional solid support.

The present compounds are used as handles in solid phase peptide synthesis to anchor a protected amino acid or peptide to a support during synthesis. The compounds have two reactive sites, represented by X and Y. They have a free reactive group, represented by "X" which reacts with the α-carboxyl group of an amino acid or peptide. The other reactive group, represented by Y, reacts with an amino group or other reactive group on the support to form a stable covalent linkage which is maintained during the synthesis process.

A method of preparing the present compounds, and reacting them with the resin support, is also the subject of the present invention. The method involves derivatizing the carboxyl function of the handle compound with an activating group, acylating the X portion of the handle with a protected amino acid or peptide, and reacting this derivative with the amino-functional resin.

Methods of anchoring protected amino acids or peptides to the support using the present compounds as handles and methods of solid phase peptide synthesis utilizing the present resin-linked handle compounds are also the subject of the present invention. In this method, an α-amino-protected amino acid or peptide is attached to the handle compound through the reactive hydroxy or halogen group represented by X, and the resulting derivative is coupled to a solid support through the activated Y component (wherein Y is an active ester). Deprotection of the α-amino groups and subsequent peptide or amino acid coupling reactions are carried out until the desired peptide or protein is formed. The resulting protected peptide or protein is then cleaved from the handle by treatment with a mild acid.

The present tris(alkoxy)benzyl ester compounds and methods of using them have several advantages over previously available handles for peptide synthesis. A covalent linkage between the handle and the resin support is formed which is stable during peptide synthesis. The linkage formed between the handle and the α-carboxyl group of the amino acid is also stable during peptide synthesis but exhibits optimal acid-lability for cleaving the peptide from the handle under mild conditions when synthesis is complete, without adversely affecting the peptide or protein which was synthesized. Fully protected proteins or peptides can be removed from the resin support without causing deprotection of the α-amino groups or side chain groups using the present handle compounds.

DETAILED DESCRIPTION OF THE INVENTION

The present invention relates to tris(alkoxy)benzyl esters and methods of using them as anchoring linkages or handles during peptide synthesis. The present compounds have an optimal balance of stability and acid-lability properties for use in peptide synthesis, particularly solid phase peptide synthesis of protected peptide acids.

The present compounds are tris(alkoxy)benzyl esters having the formula:

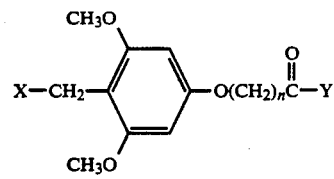

wherein n is from about 1 to about 10, X is OH, a halogen (e.g., bromine, chlorine, fluorine, iodine) or an α-carboxyl group of a protected amino acid, and Y is selected from the group consisting of: active esters, thioesters and amides. Y also represents the amide linkage to an amino-functional solid support.

The present tris(alkoxy)benzyl derivatives are used as handles or anchoring linkages to link an amino acid or peptide to a solid support for use in solid phase synthesis. The term "handle" as used herein, is defined as a bifunctional spacer molecule that on one end has a smoothly cleavable protecting group (X) and on the other end a reactive group which allows coupling to a previously functionalized support (Y). Handles serve to link the first amino acid (or peptide) to the solid phase and thereby afford maximal control over the subsequent peptide synthesis. When synthesis is complete, the handle allows the peptide or protein to be removed from the handle.

Figure 1:
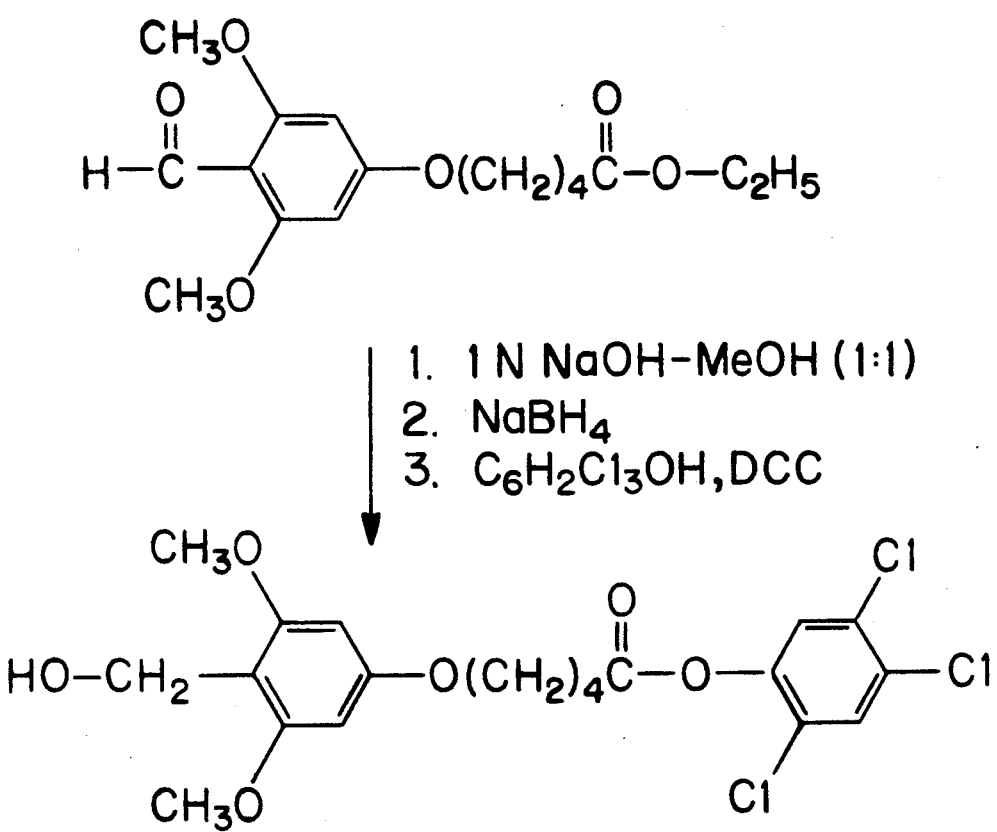
FIG. 1 is a schematic illustration of the reaction for producing 2,4,5-trichlorphenyl-5'-(4''-hydroxymethyl-3,5-dimethoxyphenoxy) valerate, shown as compound (2).
Figure 2:
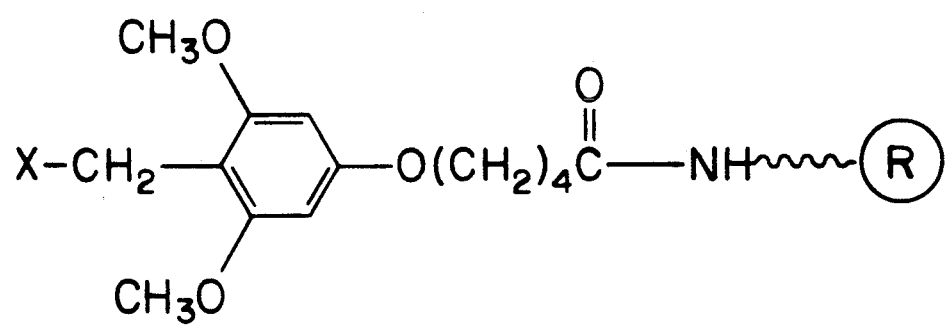
FIG. 2 is a schematic illustration of the valerate derivative of the present tris(alkoxy)benzyl ester coupled to an amino-functional resin, R.

In one embodiment of the present composition and method, a preferred compound, 5'-(4''-hydroxymethyl-3,5 dimethoxyphenoxyl)valerate, is obtained when n is 4, and X is OH and Y is an active ester. This compound can be prepared from an intermediate, 2,4,5-trichlorophenyl 5'-(4''-hydroxymethyl-3, 5-dimethoxyphenoxy)valerate (wherein Y is 2,4,5-trichlorophenyl); which can be obtained by the procedure shown in FIG. 1, starting from an available intermediate, shown as compound 1 in FIG. 1. The present compound is shown as compound 2 in FIG. 1, and is an active trichlorophenyl ester. The active ester form performs the dual role of protecting the handle carboxyl (Y) while the 4'-hydroxymethyl group (X) is being acylated, and then aclimating the same carboxyl (Y) to facilitate attachment to the solid phase.

The term "active ester" as used herein refers to compounds which activate a carboxyl group, making it more reactive with an amino group. Activating groups which can be used in the present composition and method include, in addition to 2,4,5 trichlorophenyl (TCP) esters, pentafluorophenyl (PFP) esters, pentachlorophenyl (PCP) esters and methylphenylpyrazolidone (MPP) esters. The active ester is attached quantitatively to the carboxyl group to be activated. The active ester compound is then reacted via its preactivated carboxyl group to an amino-functionalized support (about 1 equivalent) under conditions appropriate to form a covalent amide bond. Standard coupling methods for forming amide bonds can be used. For example, in one embodiment, the active ester form of a handle shown as compound 2 in FIG. 1 was attached by coupling at 25° C. for 2 hours in the presence of 1-hydroxybenzotriazole (HOBt; 2 equiv.), using N,N-dimethylformamide (DMF) as a solvent. Other methods include DCC (N,N'-dicyclohexylcarbodiimide) or DIPCO; mediated coupling A variety of amino-functional supports can be used as the solid phase, for example, macromolecules or solids, such as membranes, porous glass, silica, polystyrenes, polyamides, polydimethylacrylamides, cotton or paper. Functionalized polystyrene resins, such as amino-functional polystyrene, aminomethyl polystyrene, aminoacyl polystyrene, or p-methylbenzhydrylamine polystyrene resins can be used for this purpose. Polyethyleneglycol-polystyrene (PEG-PS) graft polymers functionalized with amino groups are particularly useful as solid phases. PEG-PS resins which can be used are described, for example, in co-pending U.S. application Ser. No. 07/760,768 filed Sep. 16, 1989 entitled "Polyethylene Glycol Derivatives For Solid-Phase Applications" by Barany et al., filed concurrently herewith, the teachings of which are hereby incorporated herein by reference.

A C-terminal protected amino acid derivative or peptide can be anchored to the nucleophilic group (represented by X) of the handle. The amino acid or peptide is generally attached to the handle prior to attachment of the handle to the solid support. The reaction can be performed by standard methods for forming peptide acid linkages, for example, by N,N'-diisopropylcarbodiimide (DIPCDI)-mediated coupling, catalyzed by 4-dimethylaminopyridine (DMAP; 0.5 equiv.), for 1 hour at 25° C., with dimethylformamide (DMF) as the solvent. The resulting derivative is then attached quantitatively to the support by standard coupling methods for forming amide linkages, as described above. The resulting support-bound handle provide a general starting point of well-defined structure for subsequent assembly of the peptide.

The resin-linked handle having the amino acid or peptide attached thereto serves as the starting point for chain elongation. Peptide synthesis can be carried out by standard tecniques such as by stepwise deprotection/coupling cycles using appropriate chemistries, to incorporate subsequent amino acid residues, thereby forming the desired peptide or protein. F. Albericio and G. Barany, *Int. J. Peptide Protein Res.*, 30:206–216 (1987); F. Albericio et al., *J. Org. Chem.*, 55:3730–3743 (1990). When synthesis is complete, the protein or peptide is cleaved from the anchoring linkage to yield the desired peptide or protein. Peptides anchored via the present handles are released readily using dilute acids, such as trifluoroacetic acid (TFA). The peptide or protein is released without affecting the protecting groups on the side-chains or Nα-terminus of the peptide. The handle anchoring linkage is stable enough, however, so that premature loss of peptide chains does not occur during peptide synthesis. Concentrations as low as 0.05% (v/v) of acid can be used to cleave the peptide from the handle. TFA having a concentration of about 0.05% to about 0.5% (v/v) is particularly useful for cleaving the peptides from the present handles.

The present handle compounds are particularly useful for the synthesis of peptide acids. Peptide acids are characterized by forming a carboxylate linkage on the Fmoc (9-fluorenylmethyloxycarbonyl) α-carboxyl terminus of the peptide.

In one embodiment of the present method, 5′-(4″-hydroxymethyl-3,5-dimethoxyphenoxy)valerate was used as the handle, attached to a PEG-PS resin support. A model tripeptide, Gly-Val-Ala, was synthesized. The linkage proved to be stable (>95% retention of peptide chains) after 24 hours, at 25° C. to HOBt (0.1M in DMF) and tert-butoxycarbonyl protected (Boc)-amino acids (0.1M in DMF). Dilute solutions of trifluoroacetic acid (TFA) in dichloromethane were used to cleave the peptide from the handle. The model tripeptide linked to the present handle was cleaved completely after 5 minutes with 0.1% TFA or after 45 minutes with 0.05% TFA, and 0.01% TFA gave 80% cleavage in 3 hours.

Demonstrations of the usefulness of the present compounds in anchoring peptides during synthesis were provided by the syntheses of several protected segments with sequences related to human gastrin-I. In this method 5′-(4″-hydroxymethyl-3,5-dimethoxyphenoxy) valerate was used as the handle, attached to a PS resin support. Three peptides, Fmoc-(Glu(OtBu))5-Ala-OH, Fmoc-(Tyr(tBu))5-Ala-OH, and Fmoc-(Lys(Boc))5-Ala-OH were each obtained in >97% purity as determined by (HPLC) after essentially quantitative cleavage with 0.1% TFA in dichloroethane (CH2Cl2), for 1 hour at 25° C. These syntheses required careful optimization of cleavage conditions to minimize side reactions. Use of the present handle resulted in higher yield and purity of the products.

A pure tryptophan-containing peptide, pGlu-Gly-Pro-Trp-Leu-OH, was also synthesized using the above-described valerate derivative. This peptide was obtained in 70–76% yield, upon cleavage with 0.05% (v/v) TFA in CH2Cl2-β-mercaptoethanol-anisole (97:2:1) or 0.05% (v/v) TFA in CH2Cl2-thioanisole-1,2-ethanedithiol-anisole (90:5:3:2), 25° C., for 1 hour. The results for all four peptides are shown in Table 1.

TABLE 1

| HAL** Anchoring for Protected Peptide Segments | | |
|---|---|---|
| Sequence | Cleavage Reagent (1 h, 25° C.) | Yield |
| Fmoc—[Glu(OtBu)]5—Ala—OH | 0.1% TFA in CH2Cl2 | ~100% |
| Fmoc—[Tyr(tBu)]5—Ala—OH | 0.1% TFA in CH2Cl2 | ~100% |
| Fmoc—[Lys(Boc)]5—Ala—OH | 0.1% TFA in CH2Cl2 | ~100% |
| pGlu—Gly—Pro—Trp—Leu—OH | 0.05% (v/v) TFA in CH2Cl2-β-mercaptoethanol-anisole (97:2:1), or 0.05% (v/v) TFA in CH2Cl2-thioanisole-EDT-anisole (90:5:3:2) | ~75%* |

*Omission of scavengers approximately halved the yield, indicating tryptophan alkylation/back-addition to support. An increased concentration of TFA did not improve the cleavage yield, either with or without scavengers.
**HAL refers to 5′-(4″-hydroxymethyl-3,5-dimethoxyphenoxy)valerate The present handle compounds are convenient to make and can be used with any amino-functionalized support. The present compounds have an optimum balance of acid sensitivity and stability, and remain entirely intact throughout the assembly of peptide chains by solid phase synthesis. Final cleavage with cocktails containing very dilute acid allows protected peptide acids to be produced in high yields and without premature removal of tert-butyl-based side-chain protecting groups, or Nα-terminal protecting groups.

The invention will now be further illustrated by the following Examples.

EXAMPLES

Example 1

Preparation of 2,4,5-trichlorophenyl-5′-(4″-hydroxymethyl-3,5-dimethoxyphenoxy)valerate Ethyl 5′-(4-formyl-3,5-dimethoxyphenoxy)valerate (13.2 g, 42.5 mmol) was dissolved in 1 n NaOH-MeOH (1:1) (100 mL) and after 10 minutes of stirring sodium borohydride (2.2 g, 60 mmol) was added portionwise over 45 minutes. After stirring two additional hours at 25° C., the solutions was chilled to 4° C., acidified with 1 N HCl to pH 5, and extracted with ethyl acetate (4×25 mL). The combined organic phases were washed with saturated aqueous NaCl (2×25 mL) and dried over MgSO4. 2,4,5-trichlorophenol (6.9 g, 35 mmol) and N,N′-dicyclohexylcarbodiimide (7.2 g, 35 mmol) were added to the ethyl acetate solution. The mixture was stirred overnight at 25° C. and then N,N-dicyclohexylurea was removed by filtration. The filtrate was washed with carbonate buffer, pH 9.5 (3.50 mL), and with saturated aqueous NaCl (2.25 mL), dried (MgSO4) and rotary evaporated. The residue was recrystallized from ethyl acetate with pentane added at 25° C. and was further chilled to −5° C. to provide a slightly orange solid (11.6 g, 25 mmol, 59% yield with respect to formyl derivative or 72% yield to trichlorophenol).

mp=101° C.-103° C.; $^1$H NMR (CDCl3) δ 7.48 (s,1H), 6.09 (s,2H), 4.66 (s,2H), 3.99(t,J=5.7, 2H), 3.76 (s,6H), 2.67 (t,J=6.7, 2H), 2.35 (broad s, 1H), 1.8–2.0 (m,4H). $^{13}$C NMR (CDCl3) 170.4 (carbonyl), 160.3 (aryl C4), 159.2 (aryl C3 and C5), 145.9 (aryl ester C1), 131.4, 131.0, 130.4 (aryl ester C2, C3, and C5), 126.2, 125.4 (aryl ester C3 and C6), 110.0 (aryl C4), 91.1 (aryl C2 and C6), 67.3) (OCH$_2$), 55.7 (CCH$_3$), 54.2 (CH$_2$OH), 33.4 (CH$_2$a to COOH), 28.5 and 21.5 (valeryl sidechain).

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A compound for use in peptide synthesis having the general formula:

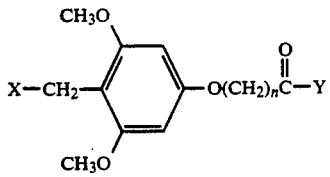

wherein n is from about 1 to about 10, X is OH, a halogen or a protected amino acid or peptide attached to the compound by its α-carboxyl group, and Y is selected from the group consisting of the activating group of an active ester, thioester and amide.

2. A compound of claim 1 wherein n is 4, X is OH and Y is an active ester.

3. A compound of claim 1 comprising an active ester of 5'-(4''-hydroxymethyl-3,5-dimethoxyphenoxy)valerate.

4. A compound of claim 1, wherein the halogen is selected from the group consisting of bromine, chlorine, fluorine and iodine.

5. A compound of claim 1, wherein the activating group of the active ester is selected from the group consisting of 2,4,5-trichlorophenyl esters, pentafluorophenyl esters, pentachlorophenyl esters and methylphenylpyrazolidone esters.

* * * * *